United States Patent
Albrektsson et al.

(10) Patent No.: US 6,610,099 B1
(45) Date of Patent: *Aug. 26, 2003

(54) FIXTURE AND PROSTHESIS INCLUDING THE SAME

(75) Inventors: Björn Albrektsson, Onsala (SE); Lars Carlsson, Kullavik (SE); Magnus Jacobsson, Göteborg (SE); Tord Röstlund, Kullavik (SE); Stig Wennberg, Angered (SE)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,987

(22) PCT Filed: Jan. 16, 1997

(86) PCT No.: PCT/SE97/00058
§ 371 (c)(1),
(2), (4) Date: Feb. 18, 1997

(87) PCT Pub. No.: WO97/25939
PCT Pub. Date: Jul. 24, 1997

(30) Foreign Application Priority Data

Jan. 19, 1996 (SE) .............................. 9600208

(51) Int. Cl.⁷ .................................................. A61F 2/36
(52) U.S. Cl. ............................... 623/23.15; 623/23.27; 623/23.11
(58) Field of Search ............................. 623/22, 16, 18, 623/22.11, 22.4, 23.11–23.47; 606/73, 80; 411/187; 408/222, 227; 433/174

(56) References Cited

U.S. PATENT DOCUMENTS

| 425,372 | A | * | 4/1890 | Dillon | 408/222 |
| 2,472,103 | A | * | 7/1949 | Giesen | 433/174 |
| 3,458,882 | A | * | 8/1969 | Kelly | 408/222 |
| 4,537,185 | A | | 8/1985 | Stednitz | 128/92 |
| 4,863,383 | A | * | 9/1989 | Grafelmann | 433/174 |

(List continued on next page.)

FOREIGN PATENT DOCUMENTS

| CA | 2122192 | 10/1994 |
| EP | 0237505 | 9/1987 |
| EP | 0595782 | 5/1994 |
| EP | 0622058 | 11/1994 |
| EP | 0552950 | 9/1996 |

(List continued on next page.)

*Primary Examiner*—Corrine McDermott
*Assistant Examiner*—Alvin Stewart
(74) *Attorney, Agent, or Firm*—White & Case LLP

(57) ABSTRACT

The invention relates to a fixture for insertion into and permanent anchorage in a cavity (32) formed in bone tissue. The fixture is made of a fixture member (2), which has an insertion end surface (10) and a cylindrical peripheral surface (6) provided with screw threads, and a plurality of circumferentially-spaced cutting recesses (9), which are formed in a forward, self-tapping end portion (7) of the threaded peripheral surface (6) adjacent to the insertion end surface (10) and which open axially into the insertion end surface (10). A plurality of circumferentially-spaced tissue-collecting and tissue-distributing grooves (17) are formed in a rear, non-self-tapping portion (8) of the threaded peripheral surface (6). The grooves (17) open radially outwards and extend at least partially in the longitudinal direction of the fixture member (2), and each groove (17) is, at a forward end thereof, connected to one of the cutting recesses (9) for collecting cut-off bone material (B) circumferentially around the inner wall of the cavity (32) during the insertion of the fixture.

19 Claims, 6 Drawing Sheets

U.S. PATENT DOCUMENTS

| | | | |
|---|---|---|---|
| 4,978,350 A | | 12/1990 | Wagenknecht ............... 606/72 |
| 4,978,506 A | | 12/1990 | Calderwood ................ 422/506 |
| 5,129,901 A | | 7/1992 | Decoste ....................... 606/65 |
| 5,147,407 A | | 9/1992 | Täger .......................... 623/22 |
| 5,370,662 A | * | 12/1994 | Stone et al. ................ 606/232 |
| 5,405,396 A | | 4/1995 | Heldreth et al. |
| 5,489,307 A | * | 2/1996 | Kuslich et al. ............... 623/17 |
| 5,562,371 A | * | 10/1996 | Reed .......................... 408/222 |
| 5,741,262 A | * | 4/1998 | Albrektsson et al. ......... 606/80 |
| 5,766,263 A | | 6/1998 | Grundei et al. |
| 5,842,865 A | * | 12/1998 | Bassett et al. .............. 433/174 |
| 5,906,616 A | * | 5/1999 | Pavlov et al. ................. 606/61 |
| 6,021,617 A | * | 2/2000 | Sheahan ...................... 52/410 |

FOREIGN PATENT DOCUMENTS

| | | | |
|---|---|---|---|
| GB | 1291470 | | 10/1972 |
| HU | 190563 | | 9/1986 |
| HU | 213975 | | 11/1997 |
| WO | 9316663 | * | 9/1993 |
| WO | 9807393 | | 2/1998 |

\* cited by examiner

FIXTURE AND PROSTHESIS INCLUDING THE SAME

TECHNICAL FIELD OF THE INVENTION

The present invention relates to a fixture for anchorage in human skeletal or bone tissue. More specifically, the invention concerns a screw-threaded, self-tapping fixture which is especially suitable for permanent anchorage of a hip-joint prosthesis in a cavity formed in the femoral collum. A fixture according to the preamble to claim 1 is known from the applicant's WO 93/16663. The invention also relates to the use of such a fixture, to a prosthesis including such a fixture, and to a method for anchoring a fixture.

BACKGROUND ART

GB 1 291 470 discloses a prosthesis fixture for anchorage in bone tissue, specifically for the mounting of a dental prosthesis in the jawbone. The fixture comprises a substantially hollow bolt which is externally threaded. The threads are intended to be screwed into a bored and pre-threaded bone cavity for permanent implantation. Adjacent to its distal end or insertion end, the bolt is provided with a number of radially-directed holes, each hole leading from the threaded outer surface into a central well. The radial holes are intended to promote an integrating growth of new-formed bone tissue during the healing process. The final ingrowth forms a "rotational lock", which prevents undesirable unscrewing and loosening of the fixture. In this document, it is also envisaged that not only the new-formed bone material, but also loose bone tissue separated as a result of the insertion of the fixture into the cavity, may participate in the integrating growth in the radial holes. The central well, in which the scraped-off bone tissue is collected, opens downwards into the distal end surface of the bolt.

EP-A1-0 237 505, which also discloses a fixture for permanent anchorage in bone tissue, specifically permanent anchorage of a dental prosthesis, teaches a modification of the above fixture according to GB 1 291 470, the purpose being to avoid an alleged drawback of scraped-off bone tissue falling down from the central well of the bolt onto the bottom of the bone cavity, thereby disturbing the osseointegration of the base of the fixture. To this end, the central well is dispensed with in the fixture of EP-A1-0 237 505, and the radial through-holes are replaced with one or more peripheral cavities communicating only with the outer cylindrical surface of the fixture. As a result, the distal end surface of the fixture is unbroken, and loose bone tissue is prevented from falling down onto the bottom of the bone cavity. The edge of each peripheral cavity in the cylindrical surface forms a sharp cutting edge for self tapping when the fixture is screwed into the bone tissue. An essential feature of this prior-art fixture is that the total tissue-collecting volume of the peripheral cavities is selected so as to contain and store all the bone tissue scraped off by the cutting edges.

U.S. Pat. No. 5,129,901 discloses a self-tapping, self-drilling, cannulated hip screw for impermanent anchorage in orthopaedic bone surgery. The screw is designed to minimise thermal necrosis and to enable efficient removal of scraped-off bone tissue (referred to as "chips") during both insertion and removal of the screw, thereby to facilitate the insertion of the screw and the subsequent removal thereof. The screw has a central bore which opens in the cutting end surface of the screw and is intended to receive a drill guide pin. The outer peripheral surface of the screw presents a relatively short threaded portion adjacent to the drilling end of the screw, and a relatively long non-threaded shank portion at its rear end. The diameter of the shank portion is smaller than the diameter of the threaded portion. A first pair of relatively short, peripheral and longitudinal cavities or "flutes" are formed and circumferentially spaced in the screw-threaded portion adjacent to the cutting end. These flutes form self-tapping cutting edges along the threads and open into the forward end surface of the screw. When the screw is drilled into the bone, the flutes direct the cut bone chips rearwards into an annular space formed between the inner wall of the drilled bone channel and the periphery of the shank portion of reduced diameter. Also, a pair of reverse cutting flutes is formed in the screw-threaded portion at an axial location rearward-spaced from the drilling end, and is arranged to cut through the bone upon unscrewing of the screw from the bone. Similar flutes are disclosed also in U.S. Pat. No. 4,537,185, cited in U.S. Pat. No. 5,129,901 mentioned above. A self-tapping, self-drilling fixation screw in U.S. Pat. No. 4,537,185 is provided with external threads intersected by flutes or grooves. The grooves form self-tapping cutting edges along the fixture, and drilling teeth are provided in a forward, non-threaded end portion of the fixture.

In WO 93/16663, which was mentioned in the introduction to this specification, a hip-joint prosthesis for permanent anchorage in the human femoral collum is disclosed. The prosthesis comprises a step-formed fixture, including a forward cylindrical first fixture member and a rear plug-like, cylindrical second fixture member rigidly connected or integrated with the first fixture member, and a prosthesis caput supported by the rear end of the fixture. Each of the two fixture members presents a screw-threaded outer surface provided with short sharp-edged cutting recesses at their insertion ends. The first fixture member is self-tapped into a relatively narrow hole drilled through the femoral collum in the cancerous bone along a predetermined axis, whereas the second member is self-tapped into a wider cylindrical cavity cut in the cancellous bone of the collum and being co-axial with the narrow hole. The axial extent of the cutting recesses is substantially less than the overall axial extent of the screw-threaded portion. More specifically, the cutting recesses of the second member are confined to a relatively short forward end portion, which tapers slightly inwards to facilitate the insertion and centering of the fixture when inserted and screwed into the wider cavity. Thus, the major part of the screw-threaded outer surface of the second member is unbroken, i.e. presents no recesses, and serves to establish an aimed-at mechanical screw connection with the inner wall of the pre-formed cavity. By contrast with the above fixture according to EP-A1-0 237 505, the cutting recesses of the second fixture member extend forwards all the way to, and open into, the forward end surface of that fixture member. By this arrangement, the bone tissue cut or scraped off by the cutting recesses will exit in the forward direction, i.e. in the insertion direction, out of the recesses and into the cavity.

As discussed in WO 93/16663, the fixture is preferably brought into engagement with the inside of the hard cortical bone of the collum in order to reduce the risk of mechanical loosening of the fixture. However, the mechanical contact between the second fixture member and the cortical bone is limited to a circumferential minor part of the screw-threaded surface. The remaining, major part of the screw-threaded surface of the second fixture member does not engage the cortical bone, but only the substantially softer cancellous bone. As a result, only a minor part of the second fixture member will be in mechanical engagement with the "hard"

bone and participate in transferring the load from the caput to the femur collum.

The present invention aims at overcoming, or at least reducing, this problem. Thus, a specific purpose of the present invention is to improve a fixture of the kind disclosed in WO 93/16663, and more generally to enhance the mechanical connection between the bone and a prosthesis fixture, thereby to accomplish a stronger permanent anchorage.

DISCLOSURE OF THE INVENTION

In accordance with the present invention, there is provided a fixture for insertion into and permanent anchorage in a cavity formed in bone tissue, comprising a fixture member, which has an insertion end surface and a cylindrical peripheral surface provided with screw threads, and a plurality of circumferentially-spaced cutting recesses, which are formed in a forward, self-tapping end portion of the threaded peripheral surface adjacent to said insertion end surface and which open axially into said insertion end surface. The fixture is characterised in that it further comprises a plurality of circumferentially-spaced tissue-collecting and tissue-distributing grooves formed in a rear, non-self-tapping portion of the threaded peripheral surface, said grooves opening radially outwards and extending at least partially in the axial direction of the fixture member, each groove opening, at a forward end thereof, axially into one of said cutting recesses for collecting cut-off bone material therefrom and guiding the same radially out of the grooves in order to distribute the collected cut-off bone material circumferentially around the inner wall of the cavity during the insertion of the fixture.

In accordance with the present invention, there is also provided a prosthesis, especially a hip-joint prosthesis, which includes such a fixture.

The invention also encompasses the use of such a fixture for anchoring a prosthesis in bone tissue, especially a permanent anchoring.

A method according to the invention for anchoring a fixture in bone tissue comprises the steps of forming a cavity in bone tissue; providing a self-tapping fixture having cutting recesses for forming inner threads in an inner wall of the cavity during an insertion of the fixture into the cavity, and having a threaded outer peripheral surface for engagement with said inner threads of the cavity; and inserting said fixture into said cavity, whereby said inner threads of the cavity are formed and said threaded outer peripheral surface of the fixture is brought into engagement with said inner threads, wherein the method is characterised in that, during the insertion of the fixture into the cavity and the formation of said inner threads, bone material cut-off by said cutting recesses for the formation of said inner threads is collected and distributed circumferentially around the inner wall of the cavity.

When the inventive fixture is inserted into a bone cavity, the forward, self-tapping portion of the fixture member will cut into the inner wall of the cavity and form threads therein for subsequent threading engagement with the rear, non-self-tapping portion of the fixture member. The bone material which is cut off during the insertion of the fixture into the cavity and initially falls into the thread-cutting recesses will be moved rearwards therefrom so as to enter the collecting grooves. This rearward movement of the bone material is due to the fact that the cavity wall exerts rearward frictional forces on loose bone material in the cutting recesses and the collecting grooves and to the fact that, once having entered the collecting grooves, the bone material is exposed to a rearward pressure exerted by bone material following after. Thus, the cutting recesses serve a twofold purpose, having a conventional thread-cutting function as well as the function of forcing new-cut bone material rearwards into the collecting grooves.

When the collecting grooves have been filled with bone material in the manner described above, continued rotation of the fixture screwed into the cavity results in the bone material in the collecting grooves being moved radially out of the fixture and being pressed against the inner wall of the cavity.

Since the cutting recesses are open in the forward direction, part of the cut-off bone material will move forwards and fall out into the cavity, i.e. in front of the front end surface of the fixture member. When this end surface approaches the bottom surface of the cavity at the end of the screwing-in operation, the amount of bone material found in the cavity will be compressed between these two surfaces. The final tightening of the fixture will therefore result in a strong, rearward material pressure exerted on the material found in the cutting recesses, this pressure being in turn transferred as a rearward pressure on to the bone material found in the collecting grooves. As a result, there is obtained a final, vigorous radial discharge of bone material from the collecting grooves during the final screwing-in operation. The fact that the cutting recesses are open in the forward direction thus ensures that there is an effective radial outflow of bone material at the end of the screwing-in operation from the collecting grooves towards the inner wall of the cavity.

Since the grooves are formed in the non-self-tapping threaded portion, the outer edges of the grooves will not act as cutting edges and, hence, there will not be any cutting-off of bone material along the grooves that might generate inwardly-directed radial compressive forces on the bone material in the grooves and thus counteract the aimed-at discharging effect.

The radial outflow of loose bone material from the fixture that is produced when the inventive fixture is screwed into the cavity will, as a result of the rotation of the fixture, be distributed circumferentially round the inner wall of the cavity. The resulting effect solves, or at least reduces substantially, the problem regarding poor anchorage in the soft cancellous bone. The automatic distribution of bone material taking place may be referred to as "autologous transplantation" of bone material. When the thread-cutting recesses cut into cortical bone, the present invention results in an advantageous displacement or "transplantation" of hard cortical bone material from that part of the cavity where the cutting recesses cut into the cortical bone to that part of the cavity which only presents softer cancerous bone. Since the cancerous bone has an almost sponge-like structure with a great many small voids and since some of these voids are open inwards towards the cavity, the hard bone material discharged from the collecting grooves will efficiently fill out these voids, thus forming a substantially tubular layer of cortical bone round the fixture. As a result, the mechanical engagement with the threads of the fixture is strengthened.

It should, however, be observed that the above autologous transplantation of cut-off bone material also occurs in the event that the fixture is threaded into cancerous bone only. In that case, the cut-off cancellous bone material is, in accordance with the invention, distributed as a compact layer round the inner wall of the cavity, hence enabling better anchorage than the untouched, spongy bone.

The main function of the collecting and distributing grooves thus is to distribute or "transplant" bone material round the fixture, thereby to strengthen the anchorage of the fixture.

The grooves further serve to prevent the emergence of necrosis of cortical bone due to the fixture damaging or blocking the normal channels for nutrient supply in the removed bone marrow and the inner periosteum. Thanks to (i) the provision of the circumferentially-spaced collecting grooves, which at least partly extend axially over a rear portion of the fixture, and (ii) the fact that these grooves will contain bone material that may constitute a breeding-ground for new bone growth, the collecting grooves with the new bone growth therein will form channels for nutrient supply to the cortical bone, thus preventing necrosis.

Further, the collecting grooves serve yet another purpose, which is known per se from the above-mentioned GB 1,291,470, namely that the ingrowth of new bone material taking place in the grooves contributes to strengthening the mechanical anchorage of the fixture.

In order to achieve efficient autologous transplantation, the total volume of the cutting recesses and the collecting grooves should be restricted and especially smaller than the total volume of bone material cut off by the thread-cutting recesses, or at least smaller than the total volume of cut-off bone material collected in the cutting recesses. This is in direct contradiction to the fixture described in the above-mentioned EP-A1-0 237 505, whose radial holes are so designed as to be able to receive and store the total volume of bone material cut off during the insertion of the fixture. Such a restriction of the bone-storage volume of the inventive fixture can be achieved by varying the parameters depth, width and length of the cutting recesses and/or of the collecting grooves.

In order to render more effective the rearward movement of the bone material into and through the grooves, the latter may preferably have a cross-section which is smaller than that of the cutting recesses, thereby to produce a "funnel effect" for the loose bone material. A given rearward pressure on the bone material in the cutting recesses is thus converted to a higher rearward pressure on the bone material in the grooves, especially during the final screwing-in operation, when the bone material found in the cavity is pressed back into the cutting recesses. Such a reduced cross-section of the grooves may be achieved by giving the grooves a smaller circumferential width than the cutting recesses. This solution is advantageous by "saving" threads needed for the mechanical engagement with the cavity wall. Another solution resulting in the above "funnel effect" is to increase the radial depth of the cutting recesses. These two solutions may also be combined.

The grooves may be perfectly axially directed in the longitudinal direction of the fixture. The grooves may also be inclined in such a direction that the rotation of the fixture contributes to the bone material moving rearwards through and out of the grooves.

In a preferred embodiment, the forward end of each recess opens into the rear part, as seen in the screwing-in direction, of the corresponding cutting recess, thereby to accomplish an effective guidance or transfer of the cut-off bone material out of the cutting recesses and into the recesses.

It is envisaged that not all the cutting recesses need be connected to a corresponding groove.

Further aspects and details of the invention will appear from the enclosed claims and the following description of two exemplary embodiments of the invention, reference being made to the accompanying drawings.

DETAILED DESCRIPTION OF PREFERRED EMBODIMENTS OF THE INVENTION

Figure 1:
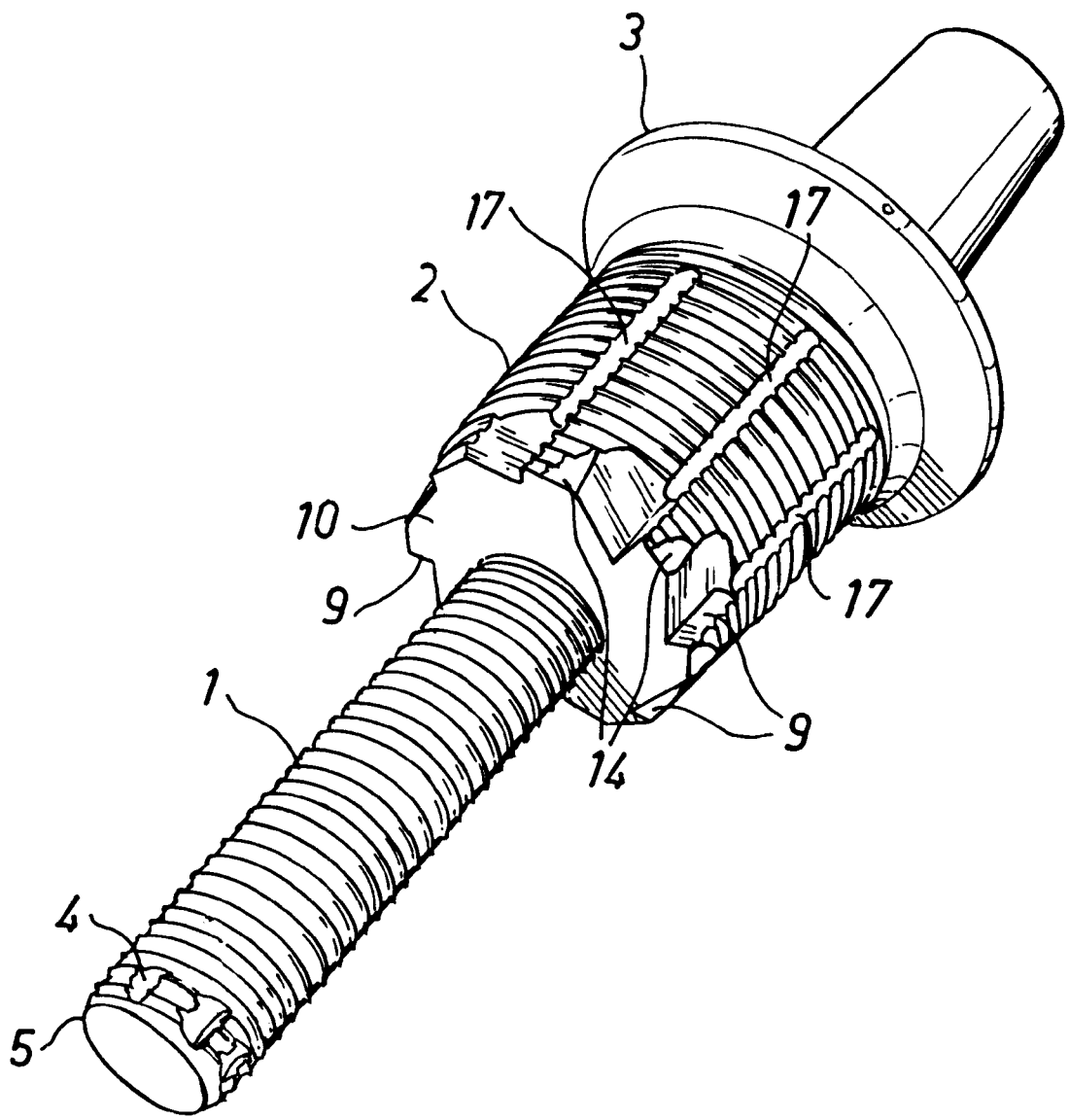
FIG. 1 is a front perspective view of a first embodiment of the fixture according to the invention, which is intended for use in a hip-joint prosthesis.
Figure 2:
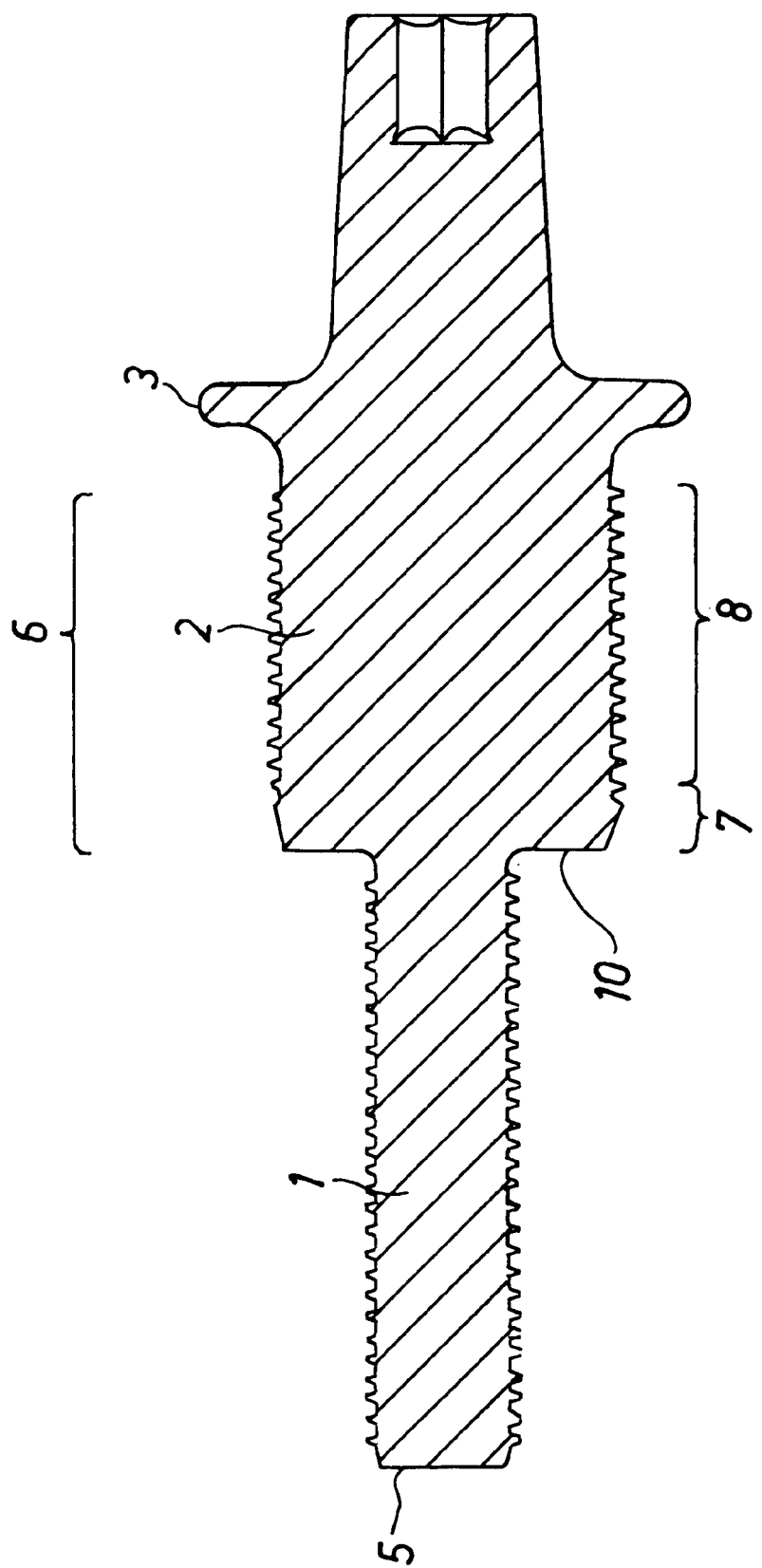
FIG. 2 is a longitudinal sectional view of the fixture shown in FIG. 1.
Figure 5:
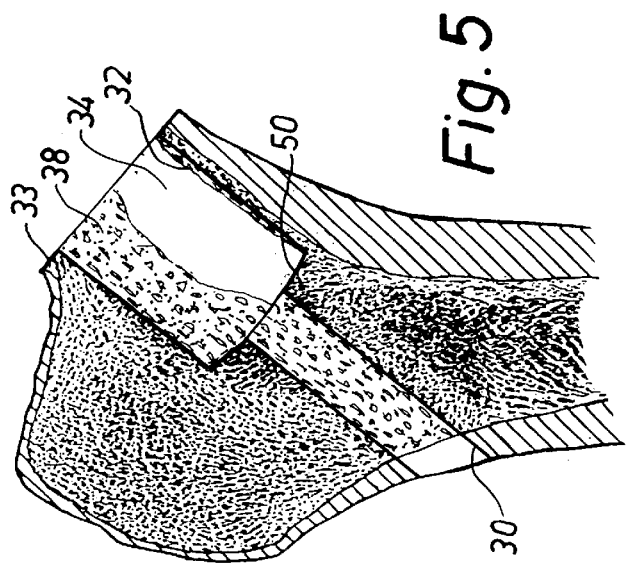
FIG. 5 is a fragmentary sectional view of the collum of a human femur, with a cavity formed therein for receiving the fixture in FIG. 1.
Figure 6:
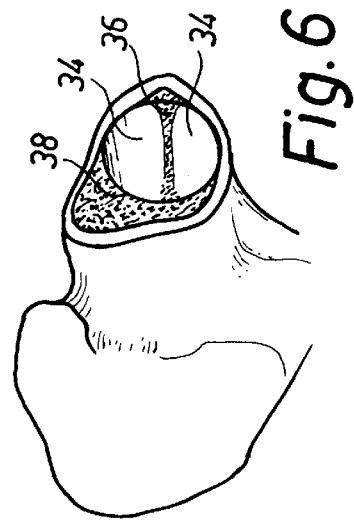
FIG. 6 is a fragmentary perspective view corresponding to FIG. 5 and illustrating the sectional form of the bone cavity.

FIGS. 1 and 2 illustrate a first embodiment of the fixture according to the invention, which is intended for use in permanent anchorage of a hip-joint prosthesis in the human femur collum. The fixture, which generally is of the type disclosed in WO 93/16663, comprises a cylindrical first fixture member 1 and a plug-like, cylindrical second fixture member 2. The second fixture member 2 is provided with a circumferential flange 3 limiting its insertion by is abutting against a cut surface (reference numeral 33 in FIG. 5) along which the head of the collum has been removed. The first fixture member 1 presents a screw-threaded outer surface provided with a number of short sharp-edged cutting recesses 4 at its insertion end 5 in order to be self-tapped into a drilled, relatively narrow hole (reference numeral 30 in FIG. 5).

The second fixture member 2 also presents a screw-threaded outer surface, the axial length of which is indicated by reference numeral 6 in FIG. 2 and which has a forward, relatively short, self-tapping end portion 7 and a rear, relatively long, non-self-tapping engagement portion 8. Eight equally-spaced, sharp-edged cutting recesses 9 are circumferentially spaced in the forward end portion 7 for self-tapping into a pre-cut bone cavity (reference numeral 32 in FIG. 5) which is coaxial with the narrow, drilled hole 30. The cutting recesses 9 open axially into a radial end surface 10 of the second fixture member 2. The forward, self-tapping end portion 7 is slightly conical in order to guide and centre the fixture during insertion thereof.

Figure 3:
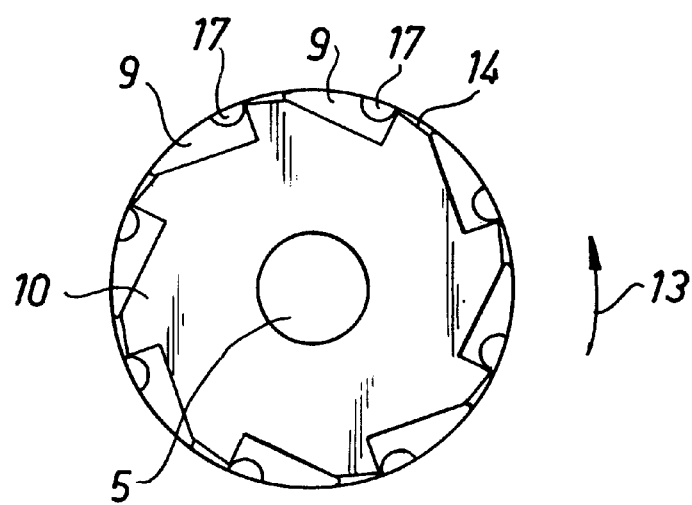
FIG. 3 is an end view of the fixture shown in FIG. 1.
Figure 4:
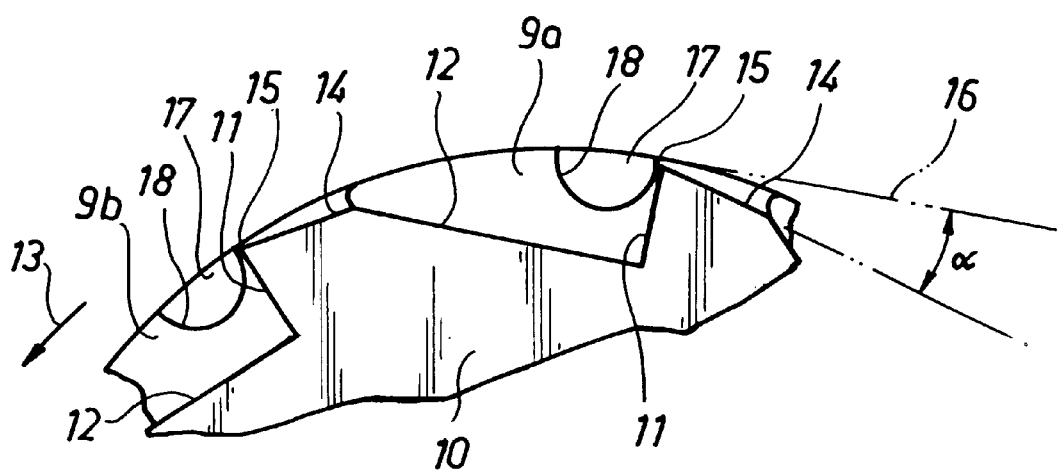
FIG. 4 is an enlarged fragmentary end view illustrating the cutting recesses and the collecting and distributing grooves in detail.

As illustrated in more detail in FIGS. 3 and 4, there are provided eight cutting recesses 9, each of which is defined by a radial wall 11 and a bottom wall 12 perpendicular thereto. The screwing-in direction of the fixture is indicated by an arrow 13. Between each pair of adjoining cutting recesses, such as the cutting recesses 9a and 9b in FIG. 4, a clearance surface 14 extends from the rear cutting recess 9a, as seen in the direction of rotation, at the front edge of the bottom wall 12, to the cutting recess 9b in front, as seen in the direction of rotation, at the cutting edge 15 thereof coinciding with the radially outer edge of the radial wall 11.

As appears most clearly from FIG. 4, each clearance surface 14 forms an angle α with a tangent 16 to the cylindrical outer surface, thereby ensuring the aimed-at self-tapping function.

Eight circumferentially-spaced, radially open collecting and distributing grooves 17 are formed in the rear, non-self-tapping portion 8 and extend in parallel with the longitudinal axis of the fixture. At the front end, each groove 17 opens into an associated cutting recess 9. The grooves 17 are so offset in the circumferential direction in relation to the cutting recesses 9 that the rear longitudinal edge of each groove 17, as seen in the screwing-in direction 13, coincides with the above-mentioned cutting edge 15 of the corresponding recess 9.

In the embodiment illustrated, each groove 17 has a substantially semicylindrical boundary wall 18 and is so dimensioned in relation to the cutting recesses 9 that the latter are wider in the circumferential direction as well as deeper in the radial direction than are the grooves 17. Thus, the cutting recesses 9 have a greater radial cross-section than the collecting grooves 17. Preferably, the transition between the cutting recesses 9 and the respective grooves 17 is softly rounded.

In the embodiment illustrated, the grooves 17 extend along essentially the entire length of the non-self-tapping portion 8, but the grooves 17 may also, within the scope of the invention, be shorter. Furthermore, collecting grooves 17 of different lengths may be provided, as may cutting recesses 9 with and without collecting grooves.

Figure 7:
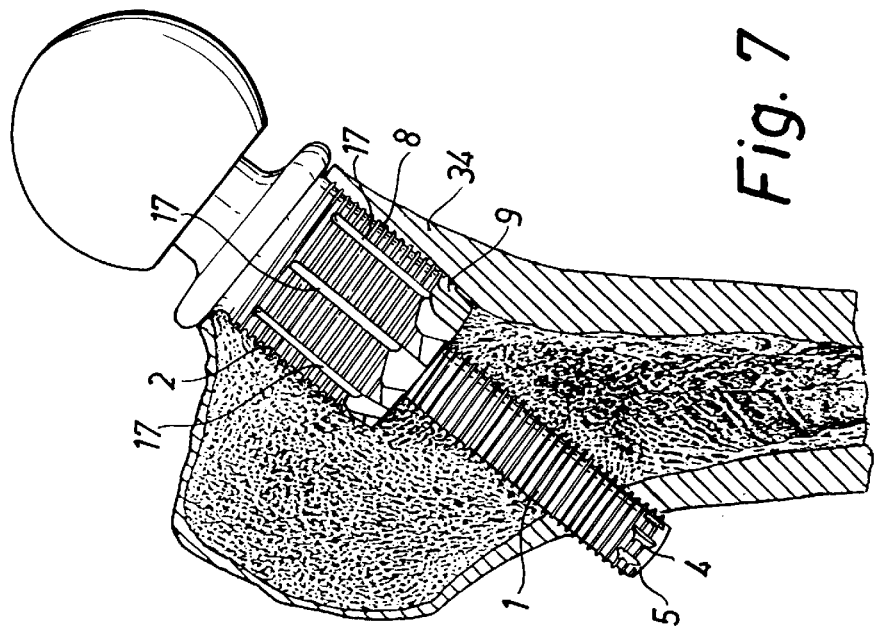
FIG. 7 is a sectional view corresponding to FIG. 5, the fixture shown in FIG. 1 being here inserted into the bone cavity.

The function of the grooves 17 will now be further elucidated with reference to FIGS. 5–8. As appears most clearly from FIGS. 5 and 6, the drilled hole 30 and the cut cavity 32 are so positioned and directed that there is, where the fixture is mounted as shown in FIG. 7, a threaded engagement between the hard cortical bone 34 and the rear non-self-tapping portion 8. The section of the cut bone surface 33 is non-circular. As appears especially from FIG. 6 in conjunction with FIG. 5, the inner wall of the cavity 32 is formed of two lower side portions of hard cortical bone 34 with an intermediate narrow "strand" 36 of soft, cancellous bone, as well as a fairly large upper portion of cancellous bone 38.

When the second fixture member 2 is threaded into the cavity 32, the cutting recesses 9 will cut off cortical bone from the areas 34, as well as cancellous bone from the areas 36 and 38. The cut-off bone material will then almost at once fill the fairly small cutting recesses 9 and, as a result of axially-directed friction against the inner wall of the cavity 32, be pressed rearwards into and be collected in the respective grooves 17, as is schematically indicated by unfilled arrows in FIG. 8. In this Figure, the cut-off bone material is designated B and indicated by a darker background. The axial screwing-in direction of the fixture is indicated by an arrow 44.

As the grooves 17 are filled, the material B subsequently supplied from the cutting recesses 9 will exert an axial rearward pressure on the material already found in the grooves 17. When the grooves 17 have thus been completely filled as a result of the combined effect of the rearward frictional forces and the rearward compressive forces, continued screwing-in and cutting-off of material will cause a radial outflow of bone material from the collecting grooves 17 and into the voids of the cancellous bone 38, as indicated schematically at reference numeral 40 in FIG. 8. In particular, cortical bone material from the areas 34 in FIG. 6 will be moved (autologous transplantation) to the cancellous areas 36 and 38, thereby to obtain round the fixture an enhanced distribution of cortical bone to strengthen the anchorage thereof.

It will be appreciated that the total volume of the cutting recesses 9 and the collecting grooves 17 should be smaller, preferably much smaller, than the total amount of bone material cut off during the screwing-in operation. This should be so in order to ensure that the grooves 17 are rapidly filled and the distribution effect activated as soon as possible.

Figure 8:
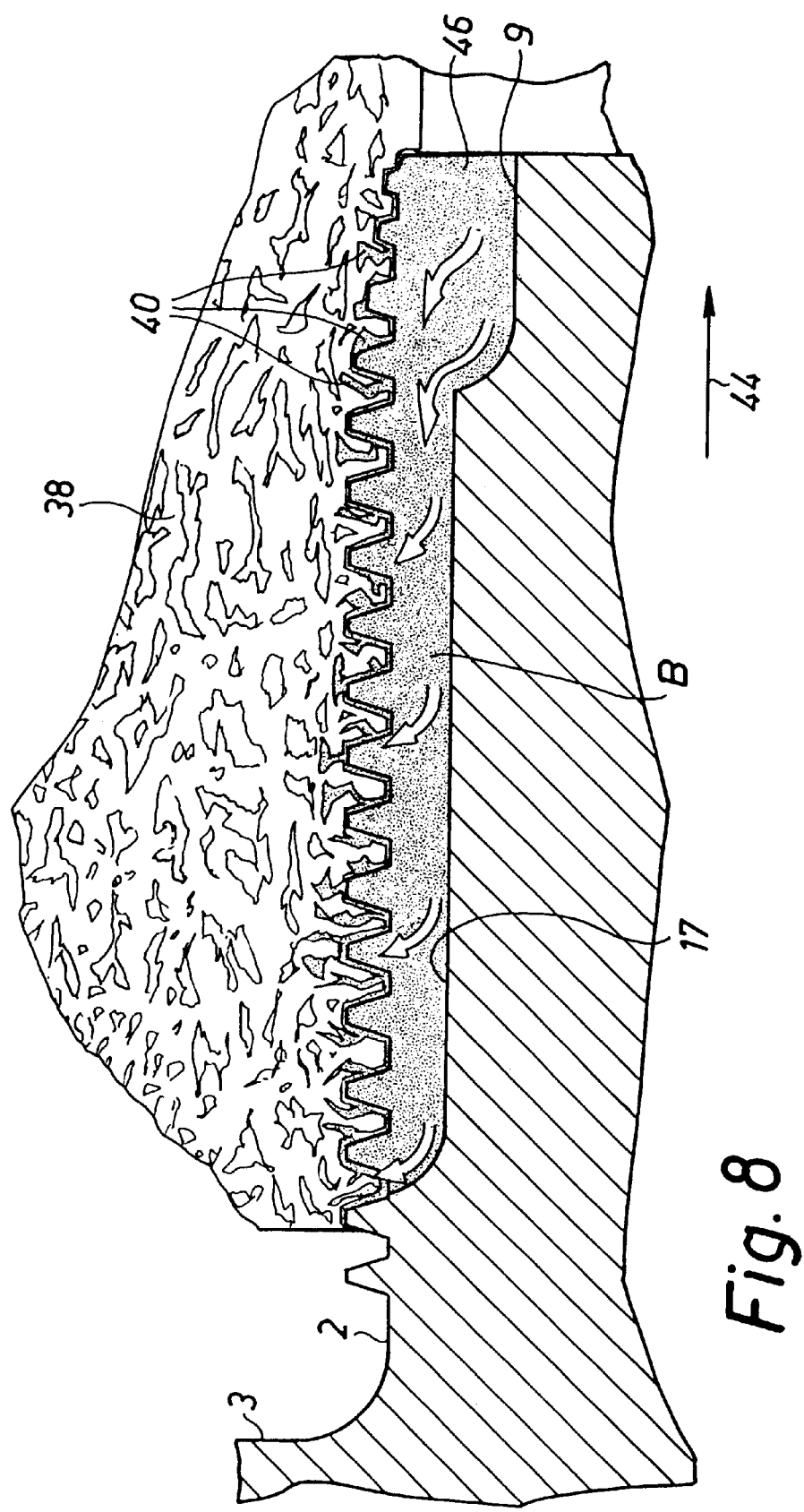
FIG. 8 is a fragmentary sectional view which schematically illustrates the function of the collecting and distributing grooves.

Since the cutting recesses 9 are open axially forwards, as is evident at reference numeral 46 in FIG. 8, part of the cut-off bone material B will fall axially forwards into the cavity 32. At the end of the screwing-in process, this bone material will be compressed between the end surface 10 and the bottom wall 50 of the cavity 32. The final tightening of the fixture will thus effectively compress this "trapped" bone material, which thereby will be strongly pressed rearwards up into the grooves 17 and be distributed over the inner wall of the cavity 32.

Figure 9:
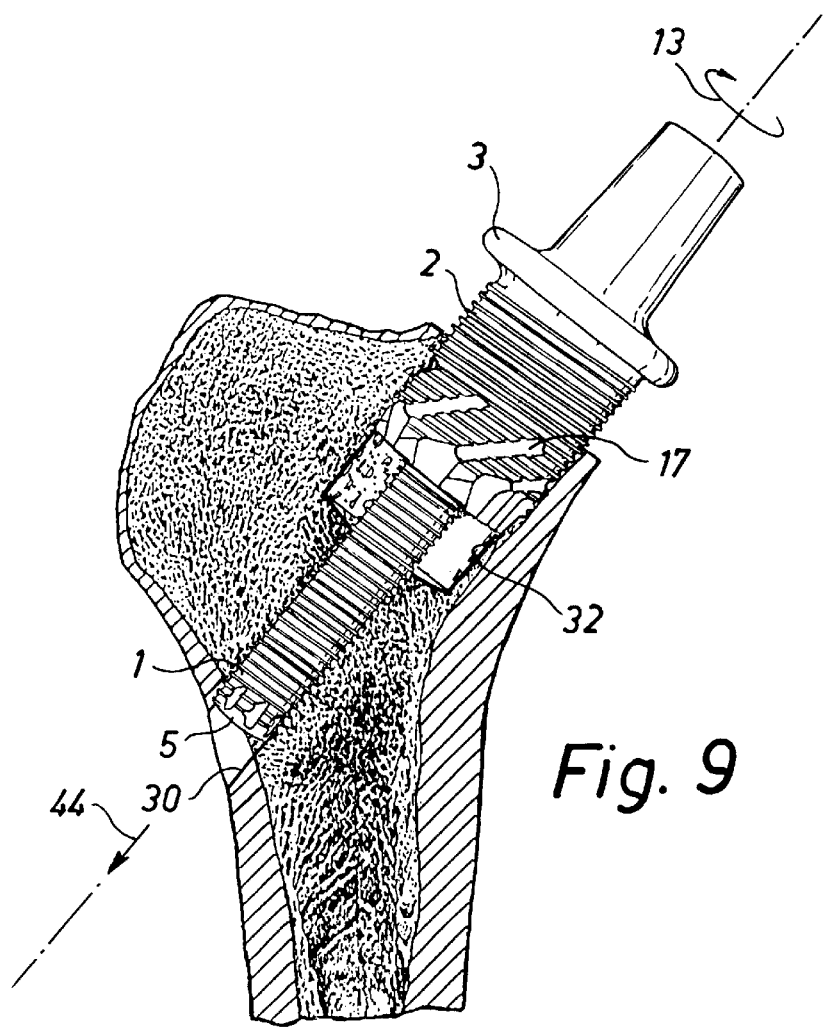
FIG. 9 is a sectional view corresponding to FIG. 5, a second embodiment of the fixture being here inserted into the bone cavity.
Figure 10:
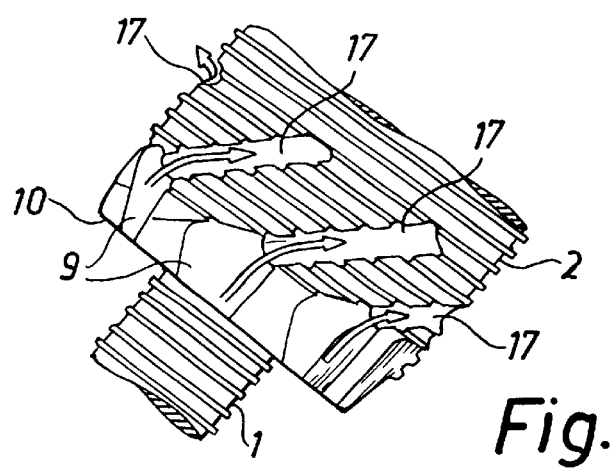
FIG. 10 is a fragmentary elevational side view of the cutting recesses and collecting and distributing grooves of the second embodiment shown in FIG. 9, illustrating the function of this second embodiment.

FIGS. 9 and 10 illustrate a second embodiment of the fixture according to the invention. This second embodiment largely corresponds to the embodiment described above, for which reason no description of equivalent parts is called for here. Thus, like elements have been given like reference numerals. In FIG. 9, the fixture is shown when partly mounted, and FIG. 10 is a broken-away enlarged view illustrating the mode of operation.

The second embodiment of FIGS. 9 and 10 differs from the first embodiment of FIGS. 1–8 in that the collecting grooves 17 are inclined in relation to the longitudinal direction of the fixture in such a manner that the rotation of the fixture during the screwing-in operation promotes a rearward movement of bone material in the grooves 17. Thus, the inlet end of the grooves 17 is situated in front of their closed rear end, as seen in the screwing-in direction 13. Furthermore, the second embodiment illustrates the fact that the grooves 17 may be shorter than in the first embodiment.

What is claimed is:

1. A prosthetic fixture for insertion into and permanent anchorage in a cavity formed in bone tissue, comprising:

a fixture member sized and configured for insertion into the cavity and permanent anchorage therein, wherein the fixture member has a longitudinal direction, an insertion end surface and a cylindrical screw-threaded peripheral surface;

a plurality of circumferentially-spaced cutting recesses, which are formed in a forward, self-tapping end portion of said screw-threaded peripheral surface adjacent to said insertion end surface and which open axially into said insertion end surface; and a plurality of circumferentially-spaced tissue-collecting and tissue-distributing grooves which are formed in a rear, non-self-tapping part of said screw-threaded peripheral surface and which open radially outwards and extend at least partially in said longitudinal direction of the fixture member, wherein each one of said grooves, at a forward end thereof, is connected to one of said cutting recesses and wherein each one of said grooves, at a rearward end thereof, is closed so that further rearward flow of the cut-off bone material within a diameter defined by the rear, non-self-tapping part of the screw-threaded peripheral surface is blocked so that the cut-off bone material collected from a cutting recess is guided radially out of the groove and distributed circumferentially around the inner surface of said cavity during the insertion of the fixture.

2. A fixture as claimed in claim 1, wherein the cutting recesses and the collecting and distributing grooves together present a total tissue-collecting volume which is smaller than a total volume of bone material cut off during the insertion of the fixture.

3. A fixture as claimed in claim 1, wherein the cutting recesses and the collecting and distributing grooves together present a total tissue-collecting volume which is smaller than a total volume of bone material collected in the collecting and distributing grooves during the insertion of the fixture.

4. A fixture as claimed in claim 1, wherein the collecting and distributing grooves have a smaller cross-section than said cutting recesses.

5. A fixture as claimed in claim 4, wherein the collecting and distributing grooves have a smaller circumferential width than said cutting recesses.

6. A fixture as claimed in claim 4 wherein the collecting and distributing grooves have a smaller radial depth than the cutting recesses.

7. A fixture as claimed in claim 1, wherein the collecting and distributing grooves are parallel with said longitudinal direction of the fixture member.

8. A fixture as claimed in claim 1, wherein the collecting and distributing grooves are so inclined in relation to said longitudinal direction of the fixture member that a rotational movement of the fixture during the insertion thereof into the cavity promotes a rearward movement of the cut-off bone material within the collecting and distributing grooves.

9. A fixture as claimed in any one of claims 1–8, wherein the collecting and distributing grooves extend, in the longitudinal direction of the fixture member, over a major portion of the non-self-tapping part.

10. A hip joint prosthesis comprising a prosthetic fixture as claimed in claim 9.

11. A method for anchoring a prosthetic fixture in bone tissue, comprising the steps of:

forming a cavity in bone tissue;

providing a self-tapping fixture sized and configured for insertion into the cavity and permanent anchorage therein, wherein the fixture member has cutting recesses for forming inner threads in an inner surface of the cavity during an insertion of the fixture into the cavity, and having a screw-threaded outer peripheral surface;

inserting said fixture into said cavity, whereby said inner threads are formed in the cavity and said screw-threaded outer peripheral surface of the fixture is brought into engagement with said inner threads; and during the said step of inserting the fixture, collecting bone material cut-off by said cutting recesses for the formation of said inner threads and distributing the thus collected bone material circumferentially around the inner surface of the cavity.

12. A method as claimed in claim 11, wherein the cavity is formed at least partly in cortical bone tissue such that cut-off cortical bone material is distributed circumferentially around the inner surface of the cavity.

13. A method as claimed in claim 11, wherein the cavity is formed in cancellous bone tissue only.

14. A method as claimed in claim 11, wherein the collected cut-off bone material is distributed out from one or more circumferentially-spaced grooves formed in a rear non-self-tapping engagement portion of the outer screw-threaded peripheral surface of the fixture, wherein the rearward end of each of said grooves is closed so that further rearward flow of the cut-off bone material within a diameter defined by the rear, non-self-tapping engagement portion of the screw-threaded peripheral surface is blocked.

15. A method as claimed in claim 14, wherein the cutting recesses and the collecting and distributing grooves together present a total tissue-collecting volume which is smaller than a total volume of bone material cut off during the insertion of the fixture.

16. A method as claimed in claim 14, wherein the cutting recesses and the collecting and distributing grooves together present a total tissue-collecting volume which is smaller than a total volume of bone material collected in the collecting and distributing grooves during the insertion of the fixture.

17. A method as claimed in claim 11, wherein said cavity presents a bottom surface, and wherein said fixture is inserted into said cavity to such an axial extent that cut-off bone material, which during a final tightening of the fixture is present in the cavity between the fixture and said bottom surface, is pressed backwards, in a direction opposite to the insertion direction of the fixture, for promoting the collection and the circumferential distribution of cut-off bone material.

18. A method as claimed in claim 17, wherein said fixture is permanently anchored in said cavity.

19. A method as claimed in claim 18, further comprising the step of attaching a prosthesis to said fixture.

* * * * *